12 United States Patent
Arend et al.

(10) Patent No.: US 12,390,632 B2
(45) Date of Patent: Aug. 19, 2025

(54) OPERATIONALLY RELIABLE BRUSHLESS DC ELECTRIC MOTOR

(71) Applicant: MAXON INTERNATIONAL AG, Sachseln (CH)

(72) Inventors: Peter Ullrich Arend, Boswil (CH); Alexis Boletis, Lucerne (CH)

(73) Assignee: MAXON INTERNATIONAL AG, Sachseln (CH)

( * ) Notice: Subject to any disclaimer, the term of this patent is extended or adjusted under 35 U.S.C. 154(b) by 358 days.

(21) Appl. No.: 17/759,781

(22) PCT Filed: Jan. 18, 2021

(86) PCT No.: PCT/EP2021/050937
§ 371 (c)(1),
(2) Date: Jul. 29, 2022

(87) PCT Pub. No.: WO2021/151708
PCT Pub. Date: Aug. 5, 2021

(65) Prior Publication Data
US 2023/0075415 A1  Mar. 9, 2023

(30) Foreign Application Priority Data
Jan. 30, 2020 (EP) .................................. 20154691

(51) Int. Cl.
*A61M 60/422* (2021.01)
*A61M 60/122* (2021.01)
(Continued)

(52) U.S. Cl.
CPC ........ *A61M 60/422* (2021.01); *A61M 60/122* (2021.01); *A61M 60/216* (2021.01);
(Continued)

(58) Field of Classification Search
CPC .. A61M 60/122; A61M 60/13; A61M 60/216; A61M 60/422; H02K 21/14;
(Continued)

(56) References Cited

U.S. PATENT DOCUMENTS 5,111,095 A * 5/1992 Hendershot ............ H02K 29/06
174/DIG. 19
5,619,085 A * 4/1997 Shramo .................... H02K 3/28
310/184

(Continued)

FOREIGN PATENT DOCUMENTS

CN  102594077 A  7/2012
DE  69629255 T2  5/2004
(Continued)

OTHER PUBLICATIONS

Translation of foreign document EP 1940007 A1 (Year: 2008).*
(Continued)

*Primary Examiner* — Alex W Mok
(74) *Attorney, Agent, or Firm* — Buchanan Ingersoll & Rooney PC

(57) ABSTRACT

The present disclosure relates to a brushless DC electric motor, such as for an actuator unit of an implant, as for a cardiac assist system, with a stator with a hollow-cylindrical iron-free winding and a rotor which can rotate relative to the stator. A shaft has a number p of pairs of permanent-magnetic poles, and the winding has a number n of three-phase systems separate from one another. The number of n three-phase systems separate from one another, is varied based on a number p of pairs of permanent-magnetic poles, and the systems are arranged in a manner spatially offset from one another by an angle of 360°/n.

15 Claims, 4 Drawing Sheets

Figure 1:
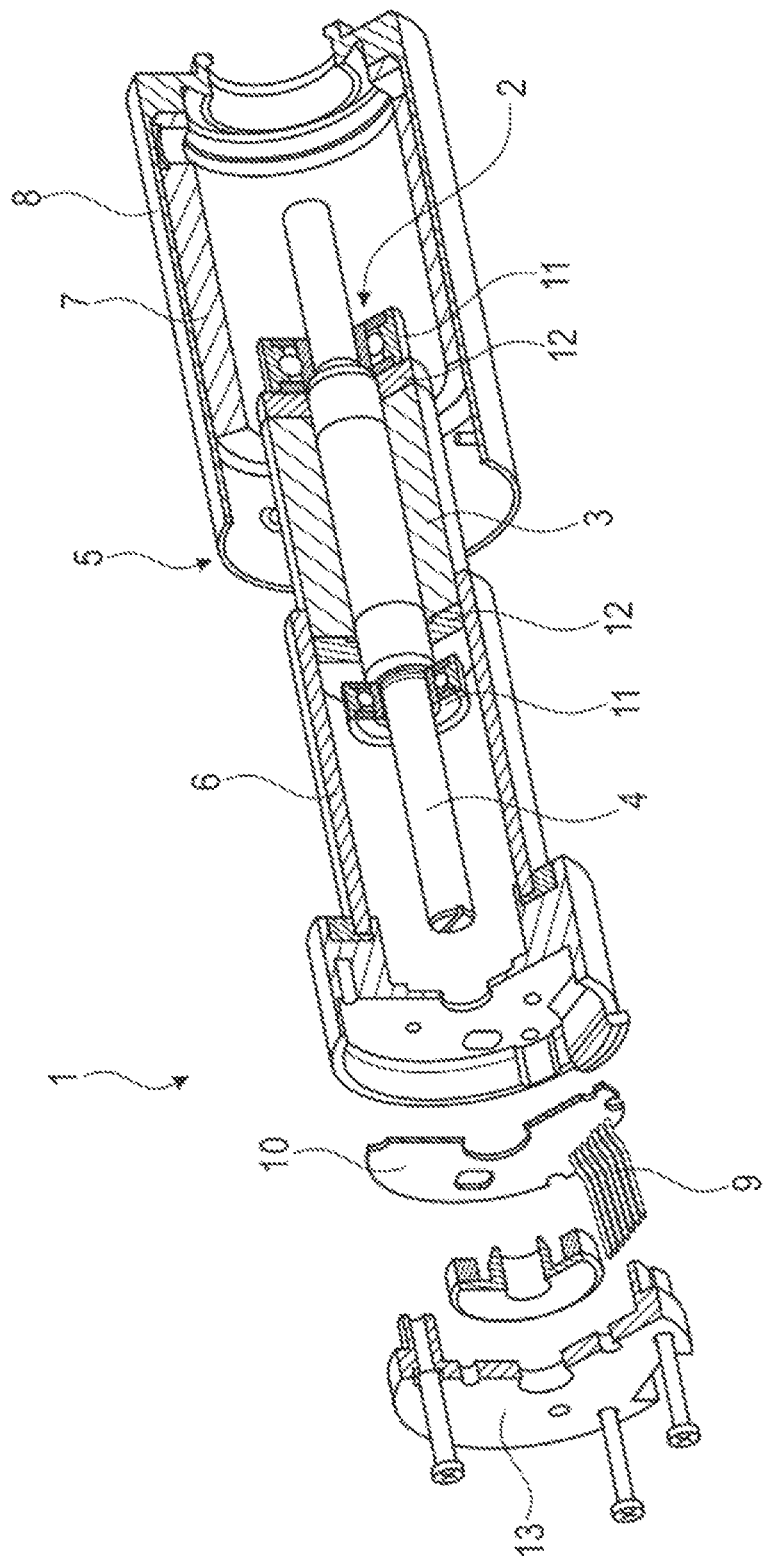

(51) Int. Cl.
  *A61M 60/216* (2021.01)
  *H02K 3/28* (2006.01)
  *H02K 3/47* (2006.01)
  *H02K 21/14* (2006.01)

(52) U.S. Cl.
  CPC ................. *H02K 3/28* (2013.01); *H02K 3/47* (2013.01); *H02K 21/14* (2013.01); *H02K 2201/03* (2013.01); *H02K 2213/06* (2013.01)

(58) Field of Classification Search
  CPC ........... H02K 2201/03; H02K 2213/06; H02K 29/08; H02K 3/18; H02K 3/28; H02K 3/47
  USPC ........................................................... 310/46
  See application file for complete search history.

(56) References Cited

U.S. PATENT DOCUMENTS

| | | | | |
|---|---|---|---|---|
| 6,100,618 | A * | 8/2000 | Schoeb | .................. F04D 5/001 310/90 |
| 7,235,906 | B2 * | 6/2007 | Carroll | .................... H02K 7/09 310/90.5 |
| 2007/0156006 | A1 | 7/2007 | Smith et al. | |
| 2012/0226097 | A1 | 9/2012 | Smith et al. | |
| 2012/0245404 | A1 | 9/2012 | Smith et al. | |
| 2014/0103850 | A1 | 4/2014 | Frank | |
| 2016/0175503 | A1 | 6/2016 | Smith et al. | |
| 2018/0351482 | A1 | 12/2018 | Kanazawa et al. | |
| 2019/0111193 | A1 | 4/2019 | Smith et al. | |

FOREIGN PATENT DOCUMENTS

| | | |
|---|---|---|
| EP | 1940007 A1 | 7/2008 |
| EP | 2922180 A1 | 9/2015 |
| EP | 3016247 A1 | 5/2016 |
| JP | H0518274 U | 3/1993 |
| JP | 2561282 Y2 * | 1/1998 |
| JP | 2015155682 A | 8/2015 |
| WO | 8403400 A1 | 8/1984 |
| WO | 2018166930 A1 | 9/2018 |

OTHER PUBLICATIONS

Translation of foreign document WO 2018166930 A1 (Year: 2018).*
Translation of foreign document JP 2561282 Y2 (Year: 1998).*
European Search Report issued in corresponding Patent Application No. EP 20 15 4691 dated Jul. 8, 2020.
International Search Report (PCT/ISA/210) with English translation and Written Opinion (PCT/ISA/237) mailed on Feb. 4, 2021, by the European Patent Office as the International Searching Authority for International Application No. PCT/EP2021/050937.
Office Action (Notice of Reasons for Rejection) issued on Nov. 26, 2024, by the Japanese Patent Office in corresponding Japanese Patent Application No. 2022-542405, and an English Translation of the Office Action. (10 pages).
Notice on the First Office Action issued on Apr. 17, 2025, by the Chinese Patent Office in corresponding Chinese Patent Application No. 202180011647.2, and an English Translation of the Office Action. (14 pages).

* cited by examiner

OPERATIONALLY RELIABLE BRUSHLESS DC ELECTRIC MOTOR

The present invention relates to a brushless DC electric motor, in particular for an actuator unit of an implant, preferably for a cardiac assist system, with a stator with a hollow-cylindrical iron-free winding and a rotor which can rotate relative to the stator and which comprises a shaft with a number p of pairs of permanent-magnetic poles, where the winding has a number n of three-phase systems separate from one another.

Brushless DC electric motors have a hollow cylindrical iron-free winding which is supplied with current by a three-phase system and which is arranged in the stator because there is no brush system that could transfer the current to a rotating winding. Accordingly, a pair of permanent-magnetic poles must co-rotate with the winding relative to the stator. The material of the pair of permanent magnets typically consists of a neodymium-iron-boron alloy in order to achieve a sufficiently high power density. The shaft provided with the pair of permanent-magnetic poles is typically mounted using preloaded ball bearings for obtaining a long service life. In order to achieve a higher power density, the rotor can be provided with several pairs of permanent-magnetic poles. A brushless DC electric motor requires electronic commutation to operate, which in principle mimics the brush system of conventional DC electric motors. Accordingly, a rotational speed-torque behavior is obtained similar to that of a conventional DC electric motor with a high starting torque and high dynamics. The main advantages of a brushless DC electric motor are the longer service life and the higher rotational speed, which are not limited by a mechanical commutation system. In particular, the hollow-cylindrical iron-free winding enables a brushless DC electric motor with reduced iron losses, with low friction and low heat losses, resulting in an extremely efficient electric motor that enables high acceleration and short response times due to its low inertia, which is particularly suitable for use with actuator units for implants and is particularly advantageous for cardiac assist pumps.

The use of brushless DC electric motors has increased steadily in the last two decades, as the electronics required for operation have become cheaper and smaller, but also due to the increased use and expansion of fields in which operationally reliable electric motors with a redundancy or with increased reliability are essential.

A redundant electric motor is known from EP 754 365 B1 and comprises a rotor with two magnetic poles arranged axially one behind the other as well as a stator composed of two windings separate from one another and arranged axially one behind the other. The windings can be controlled independently of one another and are each associated with a pair of permanent-magnetic poles. DE 31 40 034 A1 describes a redundant brushless DC electric motor in which the slotted stator windings consist of four partial strands, the sensor system for commutation consists of four sensor groups and the rotor has four pairs of poles. This redundant electric motor therefore comprises four separately controllable motor units, which make a high level of redundancy possible, but require a large installation size and a large number of individual components. A further redundant brushless DC electric motor is known from EP 2 922 180 A1 in which the winding of the stator has several winding strands that can be operated independently of one another and several independent sensor groups for detecting the rotational position of the rotor and for electronic commutation. The coil there is designed as a bifilar winding which comprises at least two separately controllable winding strands made of single wires. Although the bifilar-wound coil consists of two winding wires led in parallel that can be supplied by different voltage sources, there is a high probability in the event of a fault that the directly adjacent redundant winding system is likewise affected by an operational temperature increase or by a local weakening due to production technology. In the event of a short circuit, the affected winding wire additionally has a magnetic effect on the bifilar adjacent wire in such a way that the latter, just like the affected winding wire, is affected by the magnetic flux reduced by the opposing short-circuit current and can therefore participate in the electromechanical energy conversion only to a limited extent. Correspondingly, the bifilar-wound coil has a lower redundancy with a high negative retroactive effect of a short-circuit current, that cannot be switched off, on the remaining winding.

In addition to the many years of use of redundant electric motors in the aerospace industry, many implantable medical devices have been developed in recent years that have to be operated electrically in a fail-safe manner, for example, cardiac assist pumps. Reliable, uninterrupted operation is particularly necessary with ventricular assist devices of this type, since an interruption or a significant drop in performance can have life-threatening consequences. In addition to the redundancy of the drive unit of an implant, however, a small installation size and a low weight of the drive unit are presently also necessary aspects for enabling use in an implant. The present invention is therefore based on the object of providing an operationally reliable brushless DC electric motor which, while having a light and compact design, has sufficient redundancy to maintain operation at least to a limited extent in the event of a local fault.

This object is satisfied according to the invention in that the number n of three-phase systems separate from one another, for a number $p=1$ of pairs of permanent-magnetic poles, is 2 and, for a number $p>1$ of pairs of permanent-magnetic poles, corresponds either to an integer divisor of p, where the integer divisor is unequal to 1, or to the number p, or to twice the number p of pairs of permanent-magnetic poles (14), where the number n of three-phase systems separate from one another in the hollow-cylindrical iron-free winding is arranged in a manner spatially offset from one another by an angle of $360°/n$. An integer divisor of p is a natural number which, multiplied by another natural number, results in p. For example, if $p=6$, the numbers 1, 2, 3, and 6 are integer divisors of p. Accordingly, a number of 2, 3 or 6 three-phase systems separate from on another can then be provided, since the divisor according to the invention is unequal to 1. The spatially offset arrangement of the plurality of three-phase systems electrically separate from one another in the winding strands separate, i.e. electrically isolated from one another, leads to a segmentation of the hollow-cylindrical iron-free winding arranged around the rotor and therefore enables a fault-tolerant winding connection of a brushless DC electric motor. For a number $p>1$ of pairs of permanent-magnetic poles, at least one separate three-phase system can be associated with one or more pairs of poles consisting of a north and a south pole, whereby a decoupling of the magnetic circuits is achieved so that there is no or a reduced magnetic effect on the other three-phase systems in the event of a short circuit in one of the separate three-phase systems.

Since two three-phase systems can also be arranged opposite a pair of poles, an embodiment of the DC electric motor with one pair of poles is also possible, but preferably at least a number $p=2$ of pairs of permanent-magnetic poles is provided on the shaft, where in particular the number n of three-phase systems separate from one another corresponds to an integer divisor of p, where the integer divisor is unequal to 1, or to the number p of pairs of permanent-magnetic poles. Correspondingly, the three-phase systems that are arranged spatially offset from one another by an angle of 360°/n are each arranged disposed exactly opposite one or more pairs of poles. In the case of a rotor with only one pair of permanent-magnetic poles p=1 or with p>2 and twice the number of three-phase systems n=2·p, the three-phase systems spatially separate from one another are each arranged disposed exactly opposite a pole It is of particular advantage to have at least a number p=2 of pairs of permanent-magnetic poles be provided on the shaft and the number n of the three-phase systems separate from one another correspond exactly to the number p of pairs of permanent-magnetic poles that are spatially offset from one another in the hollow-cylindrical iron-free winding by an angle of 360°/n. In this case, the three-phase systems arranged spatially offset from one another by an angle of 360°/n are each arranged disposed exactly opposite one or more pairs of poles. This structural configuration of a brushless DC electric motor enables a high level of robustness against unforeseen faults during operation of the electric motor and enables a good degree of winding during emergency operation despite an existing fault or a disconnected winding part. Despite the high level of redundancy and fail-safety of the brushless DC electric motor that can be obtained with this configuration, conventional processes for the manufacture, testing and quality control of the electric motor can be used, as can conventional components for the power electronics and commutation logic. In contrast to the redundant electric motors known in prior art with bifilar windings in the single coils of a conventional three-phase winding or with a five- or seven-phase winding, the configuration of a brushless DC electric motor according to the invention can dispense with special and therefore cost-intensive production of the winding and the use of special power electronics and commutation logic.

The use of at least two three-phase systems spatially separate from one another in the hollow-cylindrical iron-free winding of a brushless DC electric motor according to the invention enables not only a small and compact motor configuration with a short installation length and small diameter while simultaneously having high nominal power, but also a high level of redundancy against faults in the winding system, for example, due to an operational temperature increase or a local weakening of the winding due to production technology, for which reason this brushless DC electric motor is ideally suited, for example, for a drive unit of an implant in an implantable cardiac assist system for long-term assistance of the blood circulation of the human heart. With such implantable cardiac assist systems, possible faults in a coil of the winding, but also faults in the supply line or the connection to the supply line can lead to a failure of the cardiac assist system and therefore to the demise of the patient.

An advantageous embodiment provides that, for each phase of the three-phase systems electrically separate from one another, at least a number of k=2 single coils is connected in series, where a product k·n of k single coils and n separate phase systems corresponds to twice the number of pairs of permanent-magnetic poles and where the spatial angle of the single coils, connected in series, of the respective phase of the three-phase systems separate from one another is 360°/n/k. In this embodiment, the total number of single coils of the stator therefore corresponds to twice the number of pairs of permanent-magnetic poles or the total number of rotor poles, respectively, so that the spatial angle between two single coils corresponds to the spatial angle between two rotor poles. The arrangement of the single coils spatially separate from one another increases the fault tolerance of the electric motor in the event of a winding phase failure and thereby improves the usability of the electric motor as a drive unit of an implant for which a high level of reliability against failure is required. The DC electric motor is preferably configured as a four-pole permanently excited synchronous motor with two three-phase systems electrically separate from one another in which each phase of the three-phase systems comprises two single coils connected in series and arranged at a spatial angle of 90°.

With such a four-pole synchronous motor, a high level of redundancy can already be obtained for a small installation size and low manufacturing complexity. In order to achieve the greatest possible turn density of the hollow-cylindrical iron-free winding, the single coils of the three-phase systems are provided with a rhombic winding, which is also referred to as a diamond winding.

For increased fault tolerance, two single coils, connected in series, of a phase of the at least two three-phase systems separate from one another can be electrically connected in the hollow-cylindrical iron-free winding in the opposite winding direction. The connection of two single coils in the opposite winding direction leads to a magnetic coil coupling with a north and a south pole, whereby the winding currents during emergency operation are reduced.

An expedient configuration provides that the axial positions of the at least two three-phase systems separate from one another overlap in relation to the shaft at least in certain regions. The overlapping arrangement of the axial positions of the at least two three-phase systems, which are electrically separate from one another, in the direction of the axial extension of the shaft enables a compact design of the brushless DC electric motor while having a short overall length. It is sufficient to have the magnetic fields of the three-phase systems act over a certain axial length upon a common section of the shaft. The magnetic fields of the three-phase systems, which extend perpendicular to the axial direction of the shaft, act preferably substantially only upon a common section of the shaft in order to enable a very short motor length despite a high level of redundancy.

A useful embodiment provides that the single coils of the three-phase systems, which are separate from one another, are connected to one another in a star connection, where the neutral points of the at least two three-phase systems separate from one another are preferably connected to one another. The use of a star connection for the electrical coupling of the single coils of the respective three-phase systems enables not only a higher torque constant but also the avoidance of undesirable circulating currents in the winding. The neutral points can be led out of the hollow-cylindrical iron-free winding in a simple manner individually or as a common neutral point and connected to the power electronics.

Alternatively, the single coils of the individual three-phase systems separate from one another are connected to one another in series so that an electrical coupling of the individual three-phase systems, referred to as a delta connection, is created. The delta connections can then each be connected to the power electronics. Alternatively, the single coils of the three-phase systems, that are separate from one another, of a brushless DC electric motor according to the invention are connected to one another in a single polygon connection. The delta connection of the single coils or the polygon connection of the single coils of several three-phase systems enables a higher rotational speed constant of the electric motor and therefore a reduction in the necessary supply voltage.

A separate electronic commutator, preferably an electronic block commutator, can advantageously be provided for each of the three-phase systems that are separate from one another. As a result, conventional commutators that are also used for standard motors can be employed despite the use of two three-phase systems that are electrically and spatially separate from one another. Accordingly, the development and production costs of redundant brushless DC electric motors can be reduced. Furthermore, when employing a separate electronic commutator for each of the separate three-phase systems, there is only minimal interference among the three-phase systems if one commutator fails, provided the commutators are equipped with their own voltage circuits. Consequently, the fault tolerance of the DC electric motor according to the invention can thus be improved and increased redundancy can be obtained.

Furthermore, the stator can comprise a magnetic yoke, preferably a laminated iron core arranged around the hollow-cylindrical iron-free winding. The magnetic yoke reduces the eddy-current losses and improves the power density of the DC electric motor accordingly. A laminated iron pack or a pack of iron-nickel sheet metal can be arranged around the hollow-cylindrical iron-free winding for as high-quality a yoke as possible.

A particular embodiment provides that the air gap between the rotor and the stator allows for a fluid flow through the air gap, in particular allows human blood to flow through, where the circumferential air gap is preferably larger than 15%, in particular larger than 25%, of the radius of the rotor. Such a large air gap between the rotor and the stator allows for easy employment as a drive unit of an implantable cardiac assist system and its integration into the bloodstream of patients.

Figure 2:
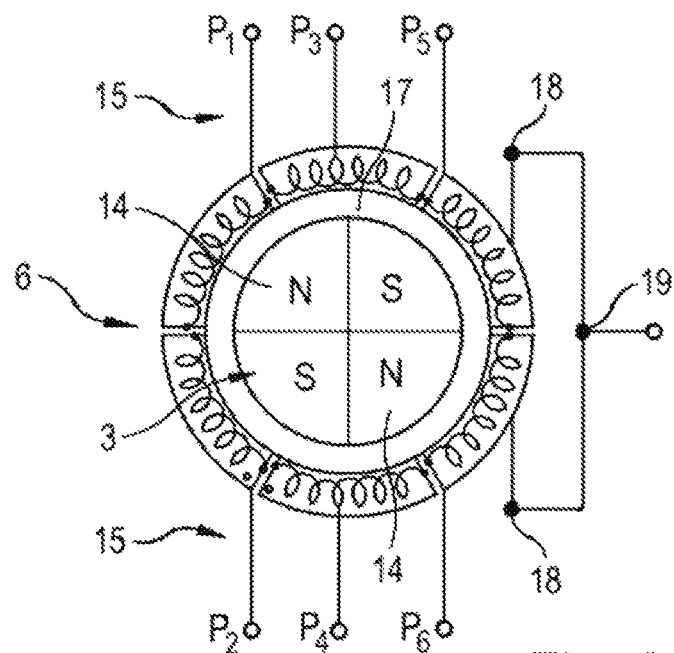
Figure 3:
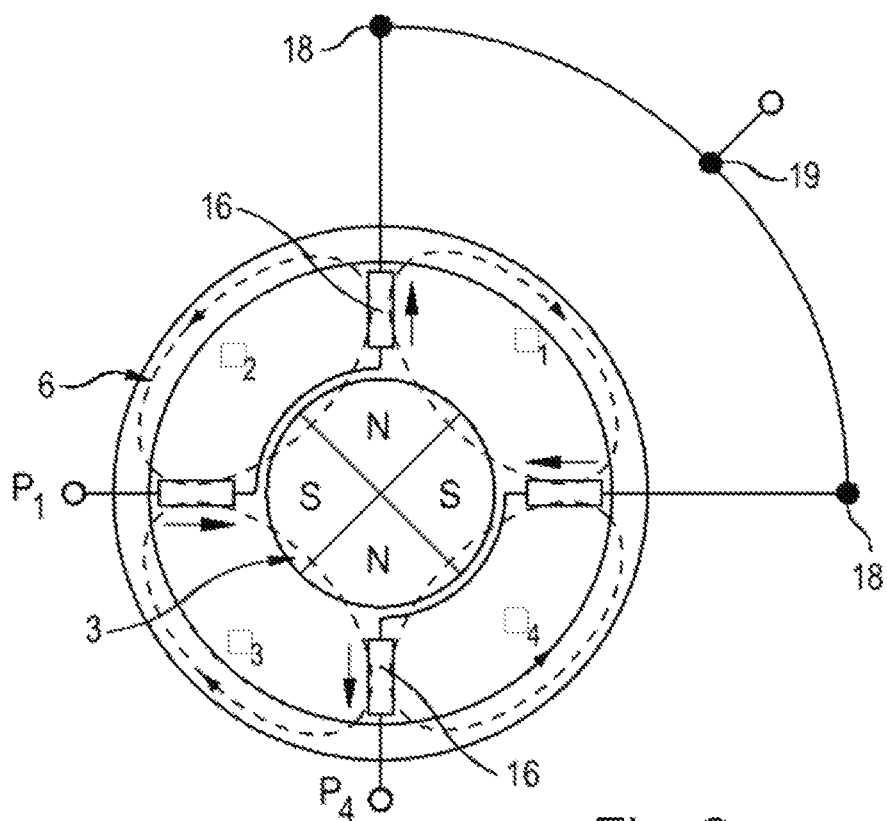
Figure 4:
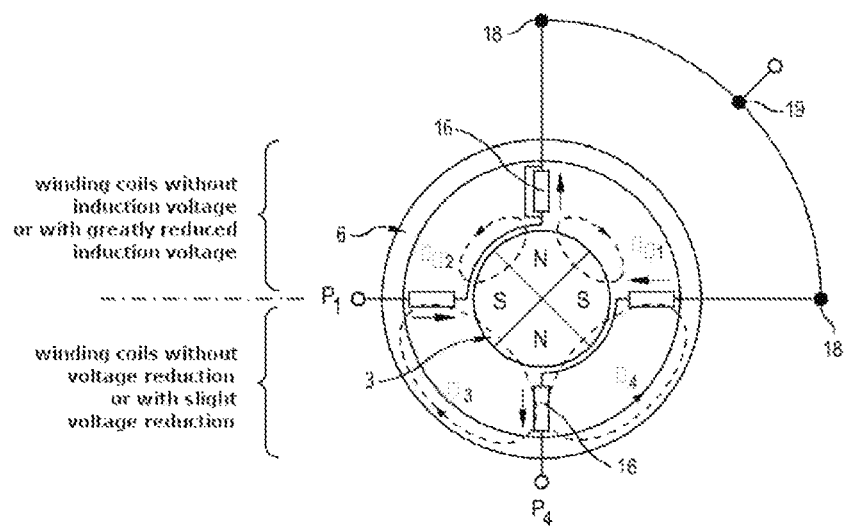
Figure 5:
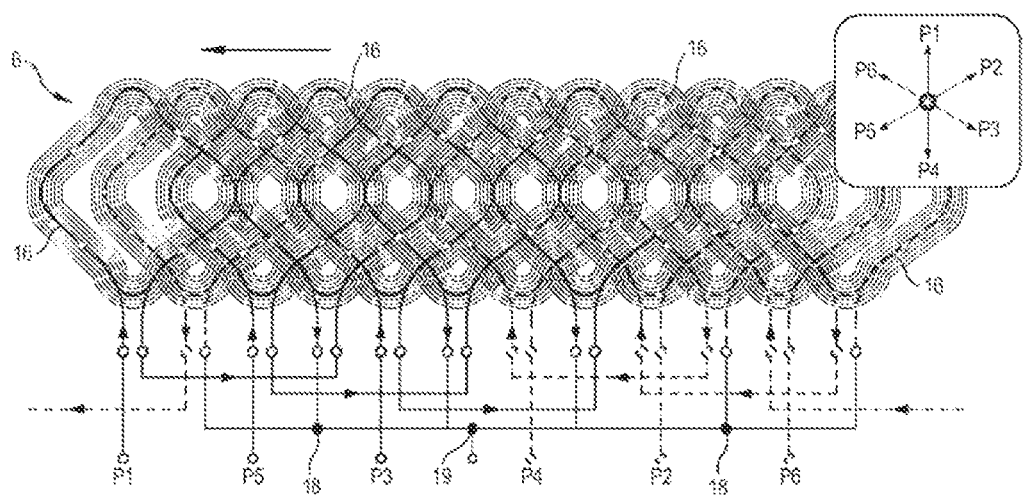

Non-restricting embodiments of the present invention shall be explained hereafter in more detail using exemplary drawings, where:

FIG. 1 shows a schematic exploded view of a brushless DC electric motor according to the invention, FIG. 2 shows a schematic representation of the coil connection of the DC electric motor from FIG. 1 with two pairs of permanent-magnetic poles and two three-phase systems, FIG. 3 shows a schematic representation of the independent magnetic fluxes for the circuit from FIG. 2 with two single coils for every phase, FIG. 4 shows a schematic representation of the independent magnetic fluxes according to FIG. 3 with an internal short between turns, and FIG. 5 shows a schematic representation of a winding configuration for the circuit from FIG. 2 with two single coils for every phase.

It applies to the following embodiments that like components are designated with like reference characters. Where a figure contains reference characters which are not explained in more detail in the associated figure description, then reference is made to preceding or subsequent figure descriptions.

The general structure of a brushless DC electric motor 1 according to the invention shall first be explained with reference to FIG. 1. The main components of this brushless DC electric motor 1 are rotatable rotor 2 with a permanent magnet 3 which is connected directly to shaft 4, as well as stator 5 in which rotor 2 is mounted to be rotatable, with a hollow-cylindrical iron-free winding 6 and yoke 7 arranged around winding 6 and connected to housing 8. Yoke 7 consists of a laminated iron pack for reducing the iron losses that occur due to rotating permanent magnet 3 of rotor 2. A printed board 10 provides for the electrical connection of winding 6 to associated power electronics by way of connecting wires 9. Sensors, for example Hall sensors, can also be arranged on printed board 10 and scan the position of permanent magnets 3 co-rotating with shaft 4.

Shaft 4 with permanent magnet 3 mounted thereon is mounted to be rotatable on two preloaded ball bearings 11. Two balancing rings 12 arranged between ball bearings 11 and permanent magnet 3 enable dynamic balancing of the rotor in that material can be removed selectively from two balancing rings 12. The balancing of the rotor by way of balancing rings 12 reduces the vibration and noise and thereby extends the service life of ball bearings 11 and entire electric motor 1, respectively, in particular at the high rotational speeds that can be reached with a brushless DC electric motor 1. Rotor 2 mounted in housing 8 can be secured with bearing flange 13 on the face side.

The connection of hollow-cylindrical iron-free winding 6 of DC electric motor 1 from FIG. 1 to a permanent magnet 3 consisting of two pairs of permanent-magnetic poles 14 and two three-phase systems 15 of winding 6, that are electrically isolated from one another, to single phases $P_1$, $P_3$ and $P_5$ or $P_2$, $P_4$ and $P_6$, respectively, is shown in FIG. 2. In addition to permanent magnet 3 with four magnetic poles, single phases $P_1$, $P_3$ und $P_5$ and. $P_2$, $P_4$ und $P_6$, respectively, each have two single coils 16 which are connected in series and arranged in winding 6 offset from one another by a spatial angle of 90°. Where a larger air gap 17 is provided between stator 5 with winding 6 and rotor 2 with permanent magnet 3, which allows for the flow of fluid, in particular for human blood to flow through. Furthermore, single phases $P_1$, $P_3$ and $P_5$ and $P_2$, $P_4$ and $P_6$, respectively, of respective three-phase systems 15 are electrically connected to one another in a star connection, where individual neutral points 18 of two three-phase systems 15 are merged with one another and are led out from winding 6 as a common neutral point 19. As an alternative to the star connection shown in FIG. 2, two three-phase systems 15 can also be connected accordingly as a six-phase polygon circuit without individual neutral points 18 or a common neutral point 19.

FIG. 3 shows a schematic representation of the independent magnetic fluxes for a DC electric motor 1 according to the invention in the star connection shown in FIG. 2. The preferred embodiment of DC electric motor 1 with a four-pole permanent magnet 3 and two three-phase systems 15 is taken as a basis here again, each with 2 single coils 16 for every phase that are connected in series and that are arranged in winding 6 at a spatial angle of 90° relative to one another. FIG. 3 shows the diagram of independent magnetic fluxes $\phi_1$ to $\phi_4$ of four single coils 16 of two associated single phases, i.e. offset by 180°, of two three-phase systems 15 separate from one another. Two single coils 16 of the respective single phases are electrically connected in opposite winding directions, resulting in a magnetic coil coupling with a north and a south pole The schematic representation in FIG. 4 shows the diagram of independent magnetic fluxes $\phi_1$ to $\phi_4$ of four single coils 16 for a faulty operating state in which a single coil 16 of winding 6 is short-circuited by an internal winding fault and ideally does not allow for any magnetic flux. In contrast to the undisturbed operating state of DC electric motor 1 in FIG. 3, a single coil 16 of single phase $P_1$ is short-circuited in an unforeseen manner by an internal fault between turns, resulting in a short-circuit current being formed that counteracts the rotor field. Magnetic fluxes $\phi_1$ and $\phi_2$ are forced out of short-circuited single coil 16 of single phase $P_1$ and must therefore close tangentially, i.e. in the circumferential direction, in air gap 17 between the surface of rotor 2 and the inner diameter of winding 6. Magnetic fluxes $\phi_1$ and $\phi_2$ therefore form only magnetic leakage flux components that are no longer detected by the winding system and can therefore no longer contribute to the electromechanical power conversion.

The magnetic coil flux consisting of magnetic fluxes $\phi_1$ and $\phi_2$ of single phase $P_1$ is reduced by ¾ to ¼ due to the short between turns. However, the magnetic coil flux in oppositely disposed single phase $P_2$ of winding 6 shows a reduction by only ¼ to ¾ of the flux that prevailed in the fault-free state in FIG. 3. After switching off short-circuited single phase $P_1$, single phase $P_2$ can still continue to be operated with a flux reduced by 25%. This relatively small impairment is due to the fact that directly adjacent pairs of poles are associated with the single phases. After switching off a faulty single phase, 10/12, i.e. about 83% of the winding system can still make a power contribution Accordingly, in emergency operation, the winding currents and, corresponding to the square of the current, the copper losses can also be reduced. Due to the higher degree of efficiency during emergency operation, DC electric motor 1 according to the invention can be classified as significantly more fault-tolerant than conventional electric motors with a simple three-phase winding 6. With DC electric motor 1 according to the invention, start-up from a standstill is also still possible during emergency operation.

The polyphase nature of DC electric motor 1 according to the invention with smaller voltage differences between adjacent single coils 16 reduces the current between adjacent single phases $P_1$ to $P_6$ during an emergency operation with internal shorts between turns. Emergency operation with an existing internal short between turns therefore causes lower additional losses and accordingly DC electric motor 1 according to the invention provides a better degree of efficiency during emergency operation. In contrast to bifilar wound windings 6, a magnetic flux can still form in the event of an internal shorts between turns in DC electric motor 1 according to the invention on more than half the circumference of winding 6 which allows for a slightly reduced voltage induction in remaining, unaffected single coils 16.

The winding configuration for DC electric motor 1 according to the invention shown in FIG. 2 is shown in the schematic representation of winding 6 with two single coils 16 for every single phase $P_1$ to $P_6$ in FIG. 5. Single phases $P_1$ to $P_6$ of two three-phase systems 15 separate from one another are connected to one another in a star connection, where neutral points 18 of at least two three-phase systems 15 separate from one another are connected to one another and can be led out of winding 6 as a common neutral point 19 and connected to power electronics. Single coils 16 of two three-phase systems 15 are configured in a rhombus-shaped winding shape in order to achieve the greatest possible turn density of hollow-cylindrical iron-free winding 6. This winding shape is also known as a diamond winding. Two single coils 16 of respective single phases $P_1$ to $P_6$ are electrically connected in the hollow-cylindrical iron-free winding in an opposite winding direction, resulting in a magnetic coil coupling with a north and a south pole and thereby to the increased fault tolerance of DC electric motor 1 according to the invention.

LIST OF REFERENCE CHARACTERS

1 DC electric motor
2 rotor
3 permanent magnet
4 shaft
5 stator
6 winding
7 yoke
8 housing
9 connecting wires
10 printed board
11 ball bearing
12 balancing rings
13 bearing flange
14 pair of poles
15 three-phase system
16 single coils
17 air gap
18 neutral points
19 common neutral point
$P_1$-$P_6$ single phases
$\phi_1$-$\phi_4$ magnetic fluxes

The invention claimed is:

1. A brushless DC electric motor comprising:
a stator with a hollow-cylindrical iron-free winding; and
a rotor arranged to rotate relative to said stator and having a shaft arranged with a number p of pairs of permanent-magnetic poles, where said winding has at least a number n=2 of three-phase systems separate from one another,
wherein the number n of three-phase systems separate from one another in said hollow-cylindrical iron-free winding is arranged in a manner spatially offset from one another by an angle of 360°/n, and where for each phase of said three-phase systems electrically separate from one another at least a number of k=2 single coils is connected in series,
wherein at least a number p=2 of pairs of permanent-magnetic poles is provided and the number n of three-phase systems separate from one another corresponds either to:
an integer divisor of p, where the integer divisor is unequal to 1, or
the number p, or
twice the number p of pairs of permanent-magnetic poles;
where a product k·n of k single coils and said n separate phase systems corresponds to twice the number of pairs of permanent-magnetic poles, and where a spatial angle of said single coils, connected in series, of the respective phase of said three-phase systems separate from one another is 360°/n/k.

2. The brushless DC electric motor according to claim 1, wherein the number n of three-phase systems separate from one another corresponds to an integer divisor of p, where the integer divisor is unequal to 1, or to the number p of pairs of permanent-magnetic poles.

3. The brushless DC electric motor according to claim 2, wherein the number n of three-phase systems separate from one another corresponds exactly to the number p of pairs of permanent-magnetic poles.

4. The brushless DC electric motor according to claim 1, wherein two single coils of a phase, connected in series, are electrically connected in said hollow-cylindrical iron-free winding in opposite winding directions.

5. The brushless DC electric motor according to claim 1, wherein the axial positions of said at least two three-phase systems separate from one another overlap in relation to said shaft at least in certain regions.

6. The brushless DC electric motor according to claim 1, wherein said single coils of said three-phase systems separate from one another are connected to one another in a star connection, where neutral points of said at least two three-phase systems separate from one another are preferably connected to one another.

7. The brushless DC electric motor according to claim 1, wherein said single coils of said individual three-phase systems separate from one another are connected to one another in series so that an electrical coupling of said individual three-phase systems, referred to as a delta connection, is created.

8. The brushless DC electric motor according to claim 1, wherein said single coils of said three-phase systems, that are separate from one another, are connected to one another in a single polygon connection.

9. The brushless DC electric motor according to claim 1, wherein a separate electronic commutator is provided for each of said three-phase systems that are separate from one another.

10. The brushless DC electric motor according to claim 9, wherein the electronic commutator is an electronic block commutator.

11. The brushless DC electric motor according to claim 1, wherein said stator comprises:
a magnetic yoke.

12. The brushless DC electric motor according to claim 11, wherein the magnetic yoke is a laminated iron pack arranged around said hollow-cylindrical iron-free winding.

13. The brushless DC electric motor according to claim 1, wherein an air gap between said rotor and said stator is configured to allow for a fluid flow through said air gap where said circumferential air gap is sized relative a radius of said rotor.

14. The brushless DC electric motor according to claim 1, in combination with:
an actuator unit of an implant configured for a cardiac assist system.

15. The brushless DC electric motor according to claim 14, wherein an air gap between said rotor and said stator is configured for human blood to flow through the gap, the gap being larger than 15% and/or larger than 25% relative to a radius of the rotor.

* * * * *